United States Patent [19]

Telikicherla

[11] Patent Number: 5,108,455
[45] Date of Patent: Apr. 28, 1992

[54] LOWER LIMB PROSTHESIS HAVING REMOVABLE RIGID AMPUTATION STUMP DRESSING

[76] Inventor: Madan M. Telikicherla, 4293 Margate La., Bloomfield Hills, Mich. 48013

[21] Appl. No.: 408,884

[22] Filed: Sep. 18, 1989

Related U.S. Application Data

[63] Continuation-in-part of Ser. No. 260,617, Oct. 21, 1988, abandoned.

[51] Int. Cl.$^5$ .................... A61F 2/60; A61F 2/62; A61F 2/64
[52] U.S. Cl. .................... 623/33; 623/27; 623/36; 623/38; 623/39
[58] Field of Search .................... 623/38, 39, 27, 33-37

[56] References Cited

U.S. PATENT DOCUMENTS

| | | | |
|---|---|---|---|
| 912,130 | 2/1909 | James | 623/35 |
| 2,464,443 | 11/1947 | Ganoe et al. | 623/36 |
| 3,707,731 | 1/1973 | Morgan | 623/38 |
| 4,128,903 | 12/1978 | Marsh et al. | 623/38 |
| 4,268,922 | 5/1981 | Marsh et al. | 623/38 |
| 4,274,166 | 6/1981 | Chambers | 623/33 |
| 4,872,879 | 10/1989 | Sharp | 623/36 |

FOREIGN PATENT DOCUMENTS

| | | | |
|---|---|---|---|
| 2103490 | 2/1983 | United Kingdom | 623/33 |

OTHER PUBLICATIONS

"Innovation Removable Rigid Dressing Technique for Below-The-Knee Amputation", Yeongchi Wu, M.D. et al., The Journal of Bone and Joint Surgery, Inc. 1979, pp. 724-729.

*Atlas of Limb Prosthetics*, American Academy of Orthopaedic Surgeons, Mosby: St. Louis, 1981 (Jul.), p. 62.

*Primary Examiner*—Randall L. Green
*Assistant Examiner*—David H. Willse

[57] ABSTRACT

A lower limb prosthesis assembly is provided for immediate post-operative applications which includes a weight-bearing prosthetic device in conjunction with a removable, size-adjustable rigid dressing for placement around a patient's amputation stump. The weight-bearing prosthetic device includes a foot-ankle assembly attached to an adjustable endoskeletal shank having adjustment means, medial and lateral uprights extending upwardly from the endoskeletal shank, and an open ended quadrilateral thigh socket attached to and located between the medial and lateral uprights. The thigh socket includes a proximal ischial weight-bearing shelf for supporting the patient without contacting the open wound of the amputation stump. The rigid dressing includes a substantially stump-shaped rigid cast portion for placement around the stump which is open-ended at the top and shaped to enclose and secure around the stump at its bottom to apply mild compression for suppressing edema of the stump. The cast portion has (a) two vertical half shells wherein each half shell has two vertically-separatable overlapping sections which are slidably adjustable for adaption to different size stumps, (b) sizing means on the cast portion for adjusting it in size circumferentially and for holding the overlapping sections together, and (c) locking means for securing the two half shells together around the amputation stump. The invention is intended to be used immediately after an amputation, as early as the first post-operative day. This provides a prosthetic device which is prefabricated, adjustable, economical and easy to use without creating any problems in the healing of the terminal surgical wound.

20 Claims, 3 Drawing Sheets

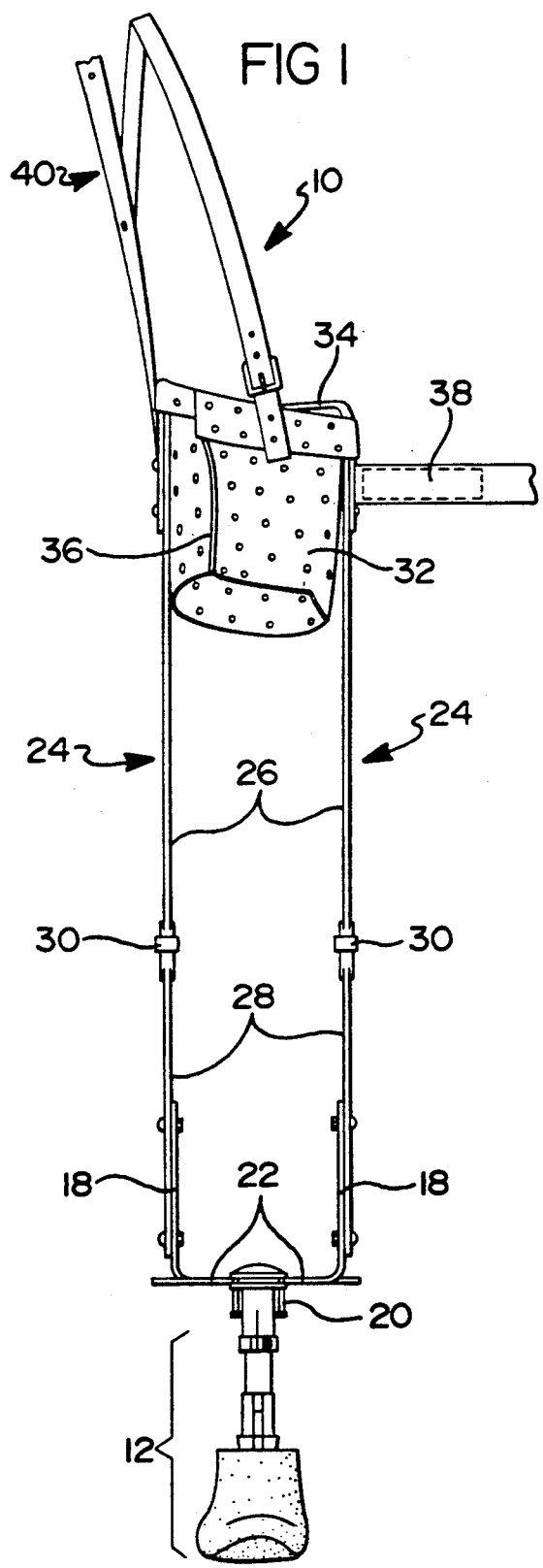
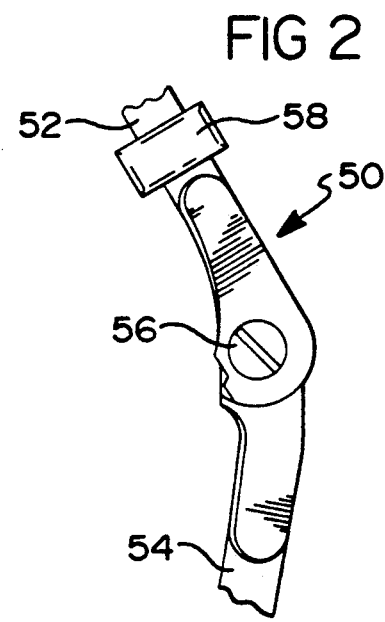
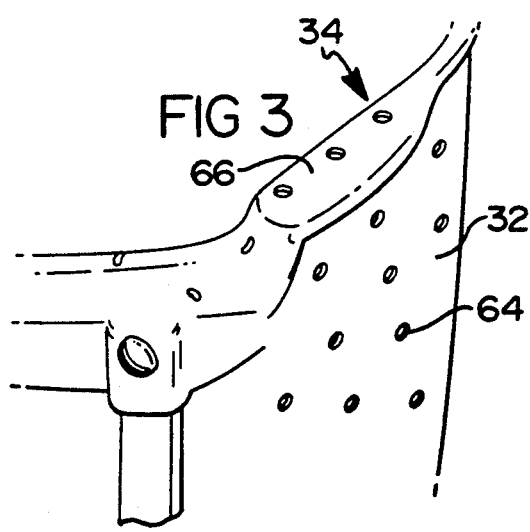

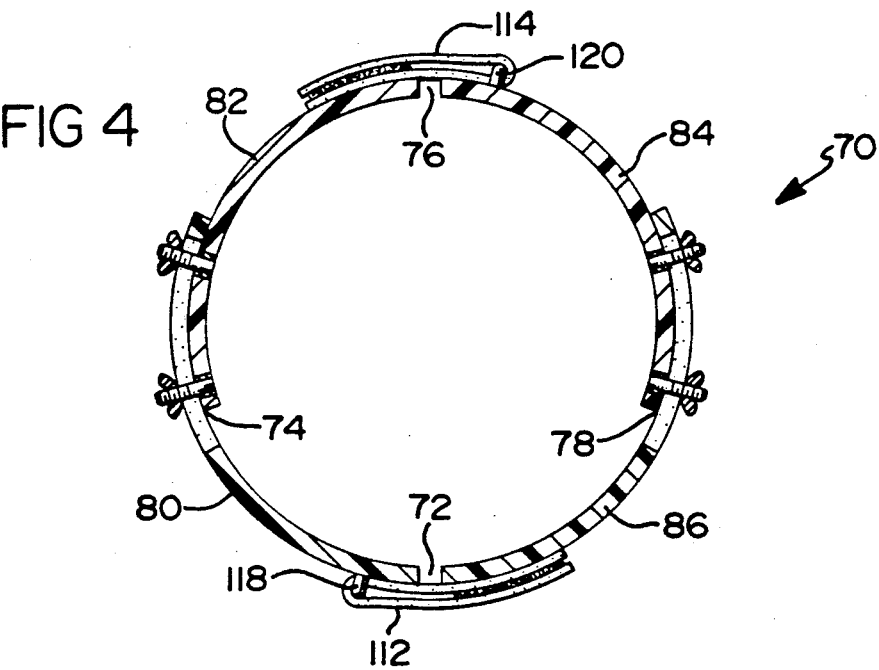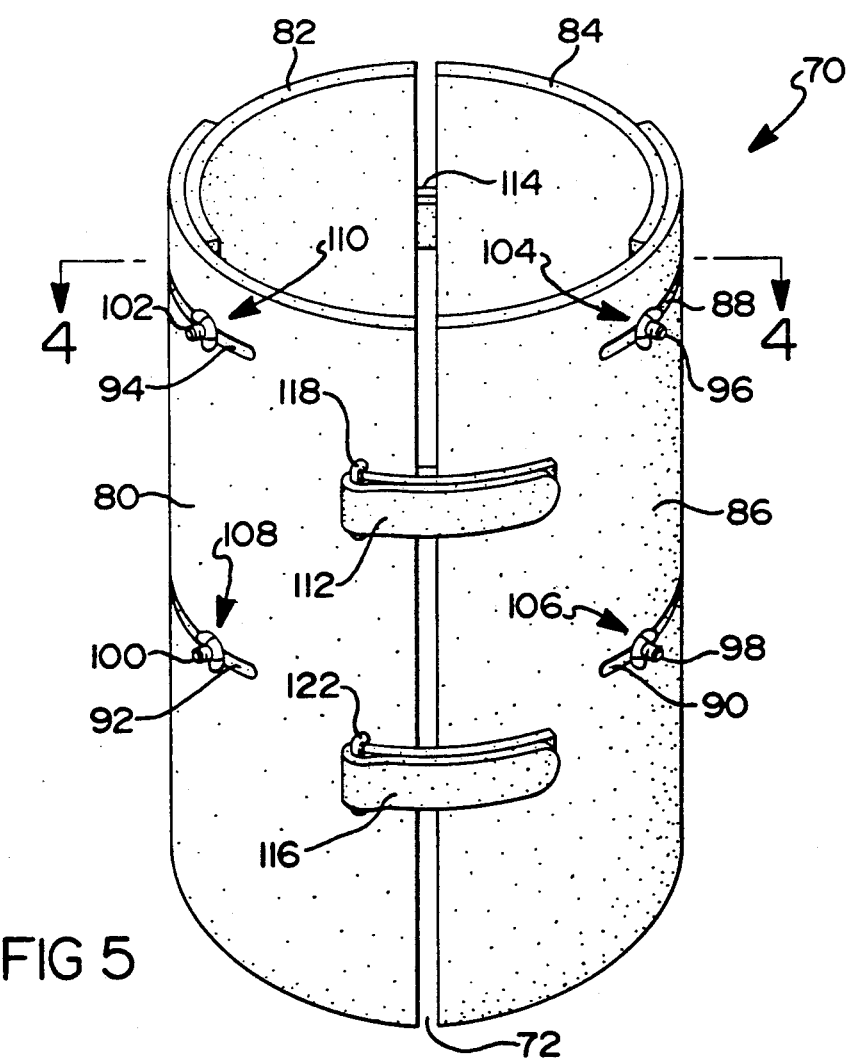

LOWER LIMB PROSTHESIS HAVING REMOVABLE RIGID AMPUTATION STUMP DRESSING

This application is a continuation-in-part of U.S. patent application Ser. No. 260,617, filed on Oct. 21, 1988.

TECHNICAL FIELD

This invention relates to rehabilitative devices especially suitable for amputated limbs and, more particularly, to a lower limb prosthetic device and rigid dressing assembly for immediate post-operative applications.

BACKGROUND OF THE INVENTION

Immediate post-operative prosthetic devices have been known to aid in the restoration of function of the dismembered limb since the 1960's. The loss of a lower extremity by amputation has profound physical and psychological consequences to the patient. Until recently, the amputation site was treated post-operatively with soft compressive dressings, nonremovable rigid dressings, or with a so-called removable rigid dressing which was made from a plaster or fiberglass cast. The reason it is considered removable is because it is pulled off the stump and then replaced after inspection. These devices allowed full weight-bearing through a temporary prosthesis after the wound had healed. Early mobilization of a patient after amputation is now generally accepted as an important part in amputation rehabilitation.

Early weight-bearing is extremely valuable in both the physical and psychological rehabilitation of the amputee. By resuming ambulation with partial or full weight-bearing at an early stage, postural reflexes can be maintained, while the residual stump may be readied for a definitive prosthetic fitting.

Many advantages are offered by fitting a prosthetic device immediately after amputation. These include early ambulation, more rapid healing of the amputation site, decreased post-operative pain and edema of the stump, shorter hospitalization times, earlier fitting of a definitive prosthesis and generally improved physical condition of the patient by preventing hypostatic pneumonia, phlebothrombosis, disuse weakness and psychological depression. The amputation team consisting of the surgeon, the physiatrist, the prosthetist and the physical therapist is aided by the immediate post-operative prosthetic device in the efficient treatment of the amputee.

In a historical perspective, as early as 1926, Le Mesurier found that a rigid dressing applied to the amputee stump immediately post-operatively initiated progressive ambulation as early as the condition of the patient permitted. Michael Berlemont of France initiated a second version of the rigid dressing for partial weight-bearing. This design was later modified by Marian Weiss of Poland for increased weight bearing. Ernest Burgess introduced the rigid dressing immediate post-surgical fitting into the United States in the 1960's. Dr. Burgess found that the closed wound of an amputation could be subjected to firm, even, pressures by use of a rigid dressing, which were carefully applied with relief for bony prominences, while attempting to avoid proximal restriction. His immediate post-surgical prosthetic devices were used on many amputation levels, including below the knee, knee disarticulation, above the knee, Syme and hip disarticulation.

However, in order to inspect the wound, the currently used prior art removable rigid dressings were merely pulled off the amputation stump, causing very great pain to the patient and generating so much friction as to traumatize the terminal surgical wound and the skin of the stump. Even though there is a felt pad between the stump and the rigid cast, the intense pain of removal and replacement discouraged patients from having their wounds inspected daily.

In addition, the prior art removable rigid dressing was applied on the operating table after the surgeon closed the amputation wound. The dressing was either a plaster cast or fiberglass. The plaster of paris reaction which occurs during the curing of the plaster or fiberglass cast generates a great deal of heat which is quite detrimental to the residual limb which already experiences compromised circulation. This is especially a problem when the amputation was performed for peripheral vascular disease.

The prior art removable rigid dressings were formed over the stump after the amputation operation. By their very nature, these rigid casts were non-adjustable and required frequent changes or entirely new casts as swelling of the stump decreased. As plaster and fiberglass casts must be custom made, they could not be reused or adjusted. The fact that they are non-adjustable means that a new cast was required when the swelling decreased to a point where the cast would have a sloppy, non-compressive fit over the stump.

Moreover, the Burgess technique requires extensive expertise for the rigid cast application, and does not allow the amputation site to be available for daily inspection. Consequently, a high incidence of stump complications became apparent, thereby requiring frequent removal of the rigid cast for inspections. The technique of Dr. Burgess was available only to patients in special medical centers where experienced prosthetists were available. As rehabilitation progresses, and the patients need to return to their physiatrists and prosthetists for continuing treatments, the immediate post-op device is used until the definitive prosthetic device is fitted.

Early attempts to solve these drawbacks included prefabricated pneumatic or plastic prosthetic devices, pneumatic air splints such as the one introduced by Morris Kerstein, and metal pylons. Although these remedies provided ease of application with ready access to the amputation site, there is no ability to flex at the knee joint, and only limited diffuse weight-bearing was possible. The air splint did not provide the capability for full weight-bearing, due to its very nature. The use of metal pylons is restricted as they are constructed of copper tubing fabricated by splitting the copper tube at one end to provide a tripod base. This base is secured to the end of a well-molded plaster rigid casting and applies pressure directly on the posterior end of the stump. Because pressure is applied directly onto the healing stump, the patients experience pain. Of the previous immediate post-operative devices, such as the pneumatic or plastic prostheses or metal pylons, none were able to provide full weight bearing. Rather, they only permitted limited weight bearing through the painful and swollen amputation stump with unhealed surgical wound in the early post-operative period.

Consequently, there is a need for an inexpensive, easy-to-fit device which is prefabricated and adjustable for the many different height and orientation requirements of individual patients. It would be advantageous to have one prosthetic device to be used for above the knee, below the knee and knee disarticulation amputations, as well as one that would allow full weight-bearing within the first few days after the amputation surgery by bypassing weight-bearing across painful and swollen stumps with a fresh or unhealed surgical wound without compromise of wound healing, skin integrity or circulation of the residual limb.

Furthermore, there is a need for a rigid dressing to be used with such a prosthetic device to reduce the incidence of distal edema, to encourage fast stump shrinkage without a cast change, to immobilize soft tissue to reduce pain and facilitate wound healing, and to prevent trauma to the stump. In addition, there is a need for a rigid dressing that is easily and painlessly removable to permit frequent observation and one which is furthermore fast and easy to apply and remove.

Accordingly, it is the primary aim of the present invention to provide a prosthetic device and rigid dressing assembly for lower limb amputation patients which is inexpensive, easy to apply without expert prosthetists, reusable, and easy to fit. The present invention is designed to provide a prosthetic device which allows for full ischial weight-bearing without compromising the wound healing.

SUMMARY OF THE INVENTION

In accordance with the present invention, there is provided an immediate post-operative ischial weight-bearing lower limb prosthesis assembly including a weight-bearing prosthetic device and a removable, size-adjustable rigid dressing for placement around the patient's amputation stump below the thigh socket. The weight-bearing prosthetic device includes a foot-ankle assembly, an adjustable endoskeletal shank having vertical adjustments for adapting the prosthesis to a particular patient, medial and lateral uprights for supporting the patient which extend upwardly from the endoskeletal shank, and an open-ended quadrilateral thigh socket attached to and located between the medial and lateral uprights. The thigh socket has an ischial weight-bearing shelf for supporting the patient without contacting the wound. Furthermore, a suspension means, such as a modified Silesian band, may be used for supporting the prosthesis on the patient, being attachable about the torso or around the waist of the patient.

Further in accordance with the present invention, a solid ankle cushion heel (SACH) may be utilized for the foot-ankle assembly. The medial and lateral uprights may include upper and lower sections connected by a knee joint which may be a manually unlocking drop lock, a bail lock, or other suitable locking mechanisms for allowing cosmesis while sitting and stability without knee buckling while standing.

The thigh socket may be made of an orthoplast-type material, as well as other conventional thermoplastic materials. The ischial weight-bearing shelf attached to the upper inner rear portion of the thigh socket may be from about ½ inch to 2 inches in width, about one to four inches in length and about ½ inch to one inch deep, depending upon the application.

The removable rigid dressing includes a substantially stump-shaped rigid cast portion for placement around the stump which is open-ended at the top and shaped to enclose and secure around the stump at its bottom to apply mild compression for suppressing edema of the stump. The cast portion has four interconnecting separatable shell sections with vertical separations extending from one end of the cast portion to the other end of the cast portion wherein the vertical separations are substantially located at 0°, 90°, 180°, and 270° of the circumference of the cast portion. The cast portion has locking means at two of the opposing vertical separations so that it can be separated into two pieces for removal and inspection of the physiological status of the stump and rejoined and locked into the patient's stump, and sizing means between the other two opposing vertical separations so that the cast portion can be adjusted in size circumferentially.

In an alternative description, the removable rigid dressing may be described as having two vertical half shells wherein each half shell has two vertically-separatable overlapping sections including an outside overlapping section and an inside overlapping section, where the overlapping sections are slidably adjustable for adaption to different size stumps. The cast portion further has sizing means for adjusting the cast portion in size circumferentially and for holding the overlapping sections together, and locking means for securing the two half shells together around the amputation stump.

BRIEF DESCRIPTION OF THE DRAWINGS

Further features and other objects and advantages of this invention will become clear from the following detailed description made with reference to the drawing in which:

FIG. 1 is a front view of a lower limb prosthetic device made in accordance with the present invention;

FIG. 2 is a detailed view of the knee joint gravity drop lock;

FIG. 3 is a perspective view of the ischial weight-bearing shelf of the thigh socket;

FIG. 4 is a cross-sectional view taken along lines 4—4 of FIG. 5 of a removable rigid dressing constructed in accordance with the present invention;

FIG. 5 is a perspective view of the removable rigid dressing;

Figure 6:
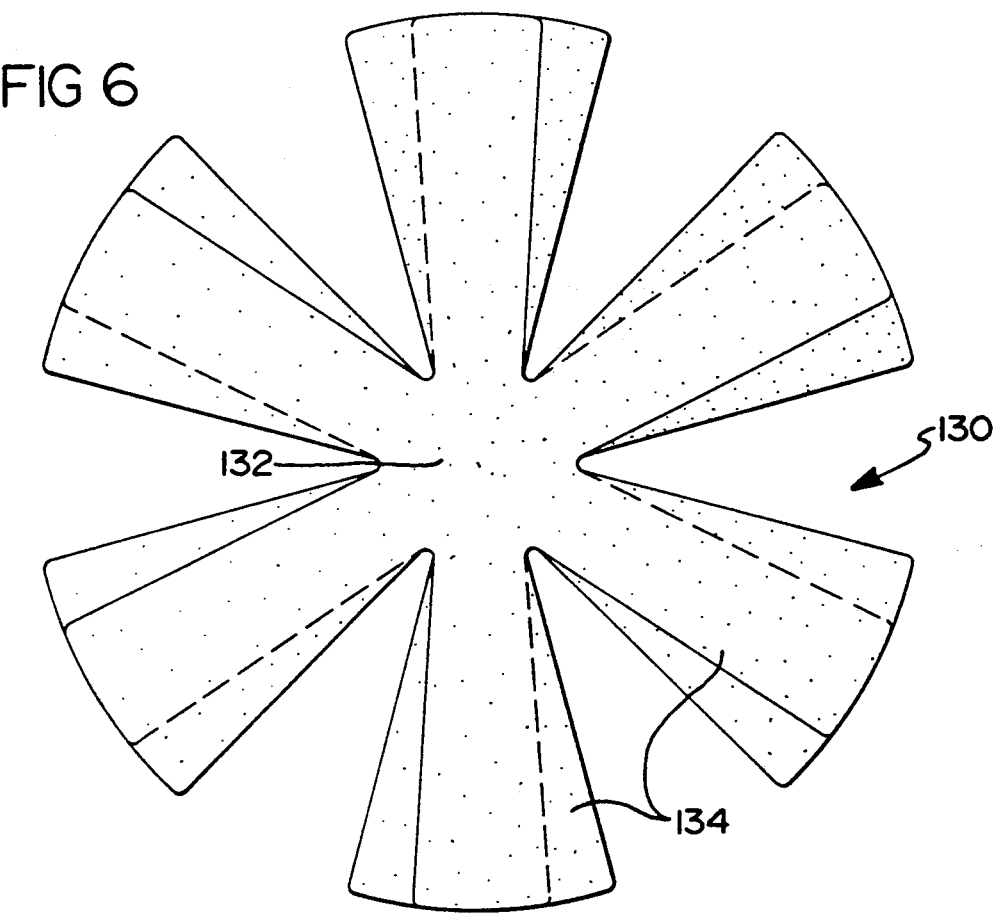
FIG. 6 is a plan view of a compressible lining in the unfolded state.

While the invention will be described in connection with a preferred embodiment, it should be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE DRAWINGS

Turning first to FIG. 1, an immediate post-operative prosthetic device is generally denoted by the numeral 10. The prosthesis 10 is composed of a foot-ankle assembly 12, and a vertically adjustable endoskeletal shank 18 attached to the foot-ankle assembly by vertical telescoping adjustment means 20. Vertical adjustment means 20 renders the prosthetic device capable of adaption to a particular patient without extensive expert prosthetist involvement. In conventional immediate post-operative rigid dressings, an expert prosthetist would tailor-make each rigid plaster casting for an individual patient. The plaster casts are not reusable, and must be removed for inspection of the stump, and then replaced with a new fresh dressing, also requiring the services of an expert prosthetist. The present invention is adjustable for the height and configuration of a patient by use of the vertical and horizontal adjustment means 20 and 22, respectively.

The foot-ankle assembly may be strictly a walking tip or may also be a solid ankle cushion heel (SACH) assembly shown as foot-ankle assembly 12. Other configurations, including a rubber walking tip, or other conventional means for contacting the floor and supporting the patient may be utilized with the present invention.

Medial and lateral uprights 24 extend upwardly from endoskeletal shank 18 for supporting the patient. In the preferred embodiment, the medial and lateral uprights 24 include upper and lower sections 26 and 28, respectively, joined and connected by knee joints 30 to allow cosmesis for the patient and to give aid in elevation from a sitting to a standing position. Knee joints 30 may have many configurations, while one preferred embodiment for the knee joint will be described further hereinbelow with reference to FIG. 2. FIG. 2 illustrates a manually unlocking drop lock using gravity to lock the leg in a standing position. A bail lock or any other conventional means may also be employed.

Referring again to FIG. 1, an open-ended thigh socket 32 is illustrated as a sheet-like material, such as orthoplast or other thermoplastic materials, and includes an ischial weight-bearing shelf 34 and an adjustment portion 36 so that the thigh socket may be adjusted to many patients. The thigh socket 32 is attached to and located between medial and lateral uprights 24 and is designed so that the top portion contacts the thigh and has a distal opening to avoid contacting the open wound, while allowing for full ischial weight-bearing to aid in rehabilitation after amputation. Thigh socket 32 is quadrilaterally-shaped as viewed from above, with all four walls extending to the same height. Socket 32 is adjustable between the anterior and posterior walls, as well as between the medial and lateral walls to allow for size variations. Thigh socket 32 may be perforated to allow air flow between the thigh of the patient and open air. Furthermore, a felt lining and/or any other conventional means may be included for giving comfort to the patient.

An important advantage of the open ended thigh socket as illustrated in FIG. 1 is the quadrilateral open-ended design which allows for full weight bearing by the ischial weight-bearing shelf 34. The ischial weight-bearing shelf 34 is designed to be placed underneath the ischial tuberosity covered by the gluteus maximus of the patient to allow for full weight-bearing as early as possible in the rehabilitation. Moreover, in order to hold the prosthetic device in place, a suspension means 40 supporting the prosthesis on the patient is shown as being attachable around the mid-torso of the patient. Various suspension means, including straps and buckles and conventional suspension means may be incorporated. It has been found to be preferable to use a modified Silesian band 38 which attaches around the waist of the patient for suspension means 40.

Referring now to FIG. 2, a manually unlocking drop lock as described hereinabove is generally illustrated by numeral 50. Upper section 52 of the medial and lateral uprights is shown connected to lower section 54 by pivot means 56. Drop lock 58 falls into position over pivot means 56 by gravity when the patient stands up, and locks upper and lower sections 52 and 54 into an upright position. As discussed hereinabove, other conventional means for knee joints are also possible, including the use of a bail lock or other lock means.

Referring now to FIG. 3, the ischial weight-bearing shelf described in FIG. 1 is shown generally as denoted by numeral 34. Thigh socket 32, including perforations 64, includes the ischial weight-bearing shelf platform 66 which is designed to be sat on by the patient. The shelf platform 66 may be from approximately ¼ inch to about 2 inches in width about 1 to 4 inches in length and about ¼ inch to 1 inch deep.

With combined reference to FIGS. 1, 2, and 3, there is disclosed a lower limb prosthesis for immediate post-operative amputation applications which provides an easily adjustable, prefabricated prosthetic device which may be adjusted for many patients, and may be reused. The open-ended thigh socket allows the open wound to remain untouched, while providing full ischial weight-bearing support through the use of the ischial weight-bearing shelf so that early ambulation may be achieved by the amputation patient. The traditional drawbacks of the rigid cast dressing are avoided because the wound is open for inspection, and interference with the wound healing is avoided. The prosthetic device of the present invention may be used in rural hospitals where expert prosthetists are not available, and may be used until a definitive prosthetic fitting has taken place. Physical and psychological benefits to the patient are realized when the patient is able to walk within the first few days after the amputation operation, generally on the first day.

FIG. 4 shows a top plan view of a removable rigid dressing including a rigid cast portion 70 which may be made of plastic, such as FIBERGLASS, or other thermoplastic material, as is commonly used in the industry. The removable rigid dressing disclosed herein is comprised of basically two parts: the rigid cast portion and the compressible lining to be sandwiched between the stump and the rigid cast portion. Discussion of the compressible lining is herein below. Rigid cast 70 has four vertical slits 72, 74, 76, and 78, which divide rigid cast 70 into four sections 80, 82, 84, and 86. Sections 80 and 82 are designed to overlap, as are sections 84 and 86. On the outside overlapping sections, sections 80 and 86, near the top and bottom ends of rigid cast 70, are horizontal slots 88, 90, 92, and 94, as is best seen in FIG. 5. Horizontal slots 88 and 90 are at the top and bottom, respectively, of section 86, and slots 92 and 94 are in section 80. Set screws 96, 98, 100, and 102 of adjustment fastening means 104, 106, 108 and 110, respectively, are slidable within and extend through slots 88, 90, 92, and 94, respectively, as shown. The slidability of the set screws within the slots allows for adjusting the diameter of rigid cast 70 to fit various stump sizes. The fastening adjustment means holds the adjoining sections securely together to maintain the desired cast size. Alternatively, the sizing means could include a belt-type device, formed of, e.g. VELCRO.

Between sections 80 and 86 are belts 112 and 116, and between sections 82 and 84 is shown belt 114, all attached to rigid cast portion 70 of the dressing. The belts are formed of material having weaving on one side which interlockingly adheres to the other side, for example, VELCRO. Belts 112, 114, and 116 loop through loops 118, 120, and 122, respectively, as shown. By unfastening the belts, rigid cast 70 is divided into two shells for easy removal and can be easily reapplied and fastened closed. Other conventional fastening means may also be employed such as belts fastened by buckles or any other suitable means.

Figure 7:
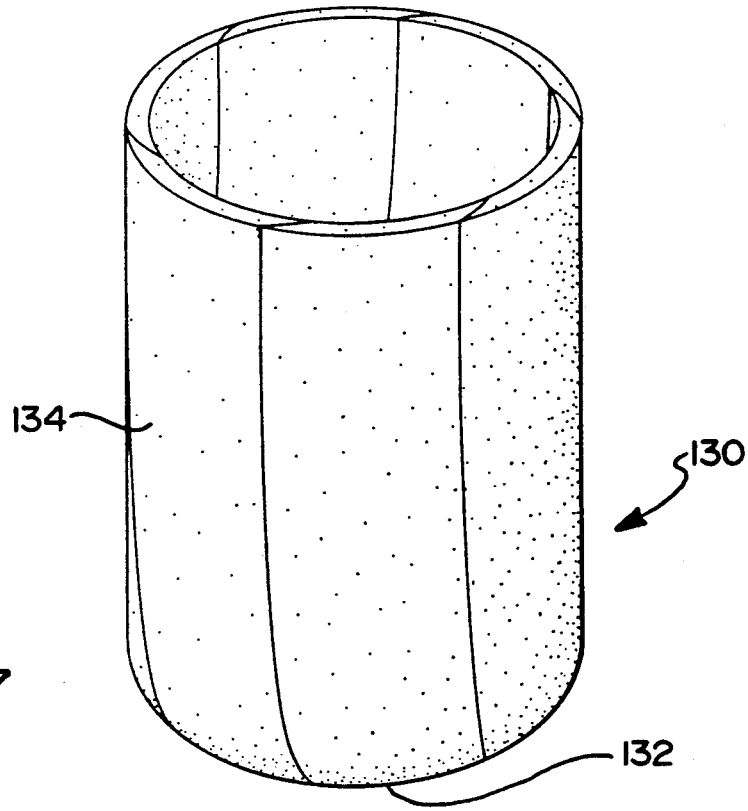
FIG. 7 is a perspective view of the compressible lining shown as it would appear once it is folded onto a patient's stump.

A compressible lining 130, as shown in FIGS. 6 and 7, is included to mildly compress the stump to suppress distal edema. This lining may be formed of, e.g., ½ inch to 1 inch thick foam rubber, having a center portion 132 which is placed on the stump end and six petals 134. The design of compressible lining 130 allows one lining to fit various stump sizes. Petals 134 have tapering edges toward adjacent petals so that when folded onto the limb and overlapped, the overlapping does not cause bulging which would cause pain due to areas of localized pressure. The compressible lining is compressed when the rigid cast portion is placed over it and expands as the swelling of the stump resolves, maintaining a snug fit of the rigid dressing around the stump without the need for additional stump socks or a new rigid dressing.

To use the rigid dressing of this invention, a freshly-sutured limb is first bandaged and covered with thin sterile stump socks, as desired. Next, the compressible lining is applied by placing the center of the lining on the end of the stump, and the petals of the lining are folded onto the stump. A rigid cast portion, which has been adjusted to fit the patient by adjusting the adjustment means while the locking means are fastened closed, is applied over the compressible lining. The rigid cast portion, by providing uniform, controlled compression on the stump, reduces the swelling of the stump post-operatively and caused during dependent positions while standing and walking. The petals may include a light adhesive on the surfaces to be placed adjacent one another for ease of application.

Next, an appropriately-sized proximal contact lower limb prosthesis is fitted on the patient about the rigid dressing. The prosthesis can be adjusted in size vertically and horizontally before or after being fitted on the patient so that the prosthesis does not conflict with the rigid dressing already in place.

The rigid cast portion of the dressing is removable for inspection of the wound, as desired, taking only minutes to remove and reapply, without having to use a new cast or lining. The rigid dressing is designed to be so simple to apply that little or no training is required for application or removal. The hospital or facility can stock a few sizes of rigid cast portions and linings to fit various patients and wound types. Since the rigid casts are adjustable in size circumferentially, only a few sizes of casts are required to fit several sizes of patients. In addition, if the rigid cast portion is formed of sterilizable material, for example, FIBERGLASS, the cast can be sterilized and reused.

Various lower limb amputation types, such as below-the-knee amputations and knee disarticulations, are able to tolerate longer rigid dressings than above-the-knee amputations because interference with the quadrilateral socket of the prosthesis will be minimized. Consequently, shorter rigid dressings are used for above-the-knee amputations to avoid interference with the quadrilateral socket of the prosthesis. The rigid dressing can be made in one length and cut to fit various size patients and types of amputations. Likewise, a shortened thigh socket may be useful for above-the-knee amputees if the stump is too short to comfortably accommodate both a shortened removable rigid dressing and a normally-sized thigh socket.

Thus, it is apparent that there has been provided, in accordance with the invention, an immediate post-operative ischial weight-bearing lower limb prosthesis and rigid dressing assembly that fully satisfies the objects, claims and advantages as set forth above. While the invention has been described in conjunction with the specific embodiment thereof, it is evident that many alternatives, modifications and variations will be apparent to those skilled in the art in light of the foregoing description. Accordingly, it is intended to embrace all such alternatives, modifications and variations as they may fall within the spirit and broad scope of the appended claims.

I claim:

1. A lower limb prosthesis assembly for immediate post operative amputation applications, comprising:
    (A) a weight-bearing prosthetic device including
        (i) a foot-ankle assembly;
        (ii) an adjustable endoskeletal shank attached to the foot-ankle assembly including vertical and horizontal adjustment means for adapting said weight-bearing prosthetic device to a particular patient;
        (iii) medial and lateral uprights extending upwardly from the endoskeletal shank for supporting the patient, said uprights having upper and lower sections connected by a knee joint;
        (iv) an open ended quadrilateral thigh socket attached to and located between the medial and lateral uprights, said thigh socket having an ischial weight-bearing shelf for supporting the patient without contact to the wound;
        (v) a suspension means for supporting said weight-bearing prosthetic device on the patient, said suspension means being attachable around the torso of the patient; and
    (B) an independent removable, size-adjustable rigid dressing for placement around the patient's amputation stump below said quadrilateral thigh socket, said rigid dressing including
        (i) a substantially stump shaped rigid cast portion for placement around said stump, said cast portion being open-ended at the top and shaped to enclose and secure around the stump at its bottom to apply mild compression for suppressing edema of the stump, said cast portion having four interconnecting separatable shell sections with vertical separations extending from one end of the cast portion to the other end of the cast portion wherein said vertical separations are substantially located at 0°, 90°, 180°, and 270° of the circumference of said cast portion, said cast portion having
            (a) locking means at two of the opposing vertical separations so that said cast portion can be separated into two pieces for removal and inspection of the physiological status of the stump and rejoined and locked onto the patient's stump, and
            (b) sizing means between the other two opposing vertical separations so that said cast portion can be adjusted in size circumferentially.

2. The lower limb prosthetic assembly of claim 1, further comprising a compressible lining for placing between the stump and said cast portion to assist in applying mild compression to the stump and maintain a close fit after stump shrinkage.

3. The lower limb prosthetic assembly of claim 2, wherein said compressible lining comprises a flat flower-like piece of compressible material having a substantially circular middle to be placed over the end of the stump and having a plurality of petals to be overlappingly folded over the stump.

4. The lower limb prosthetic assembly of claim 3, wherein the thickness of each of said petals is tapered toward an adjacent petal so that when said petals are folded on the stump and overlapped the overlapped petals cover the stump with a substantially uniform thickness of compressible material.

5. In a lower limb prosthetic assembly for immediate post-operative amputation applications having a weight-bearing prosthetic device which includes a foot-ankle assembly; an adjustable endoskeletal shank attached to said foot-ankle assembly including vertical and horizontal adjustment means for adapting said weight-bearing prosthetic device to a particular patient; medial and lateral uprights extending upwardly from said endoskeletal shank for supporting the patient, said uprights having upper and lower sections connected by a knee joint; an open ended quadrilateral thigh socket attached to and located between the medial and lateral uprights, said thigh socket having an ischial weight-bearing shelf for supporting the patient without contact to the wound; and a suspension means for supporting said prosthetic device on the patient, said suspension means being attachable around the torso of the patient, wherein the improvement comprises:

an independent removable, size-adjustable rigid dressing for placement around the patient's amputation stump below said quadrilateral thigh socket, said rigid dressing including a substantially stump-shaped rigid cast portion for placement around said stump, said cast portion being open-ended at the top and shaped to enclose and secure around the stump at its bottom to apply mild compression for suppressing edema of the stump, said cast portion having
  (a) two separatable vertical half shells wherein each half shell has two vertically-separatable overlapping sections including an outside overlapping section and an inside overlapping section, said overlapping sections slidably adjustable for adaptation to different size stumps,
  (b) sizing means on said cast portion for adjusting said cast portion in size circumferentially and for holding said overlapping sections together, and
  (c) locking means for securing said two half shells together around the amputation stump.

6. The lower limb prosthetic assembly of claim 5, wherein said locking means comprises a belt-like locking device.

7. The lower limb prosthetic assembly of claim 5, wherein said locking means comprises belt-like strips of material attached to said cast portion which adhere to each other via interlocking weaving.

8. The lower limb prosthetic assembly of claim 5, wherein said sizing means comprises a belt-like locking device.

9. The lower limb prosthetic assembly of claim 5, wherein said sizing means comprises belt-like strips of material attached to said cast portion which adhere to each other via interlocking weaving.

10. The lower limb prosthetic assembly of claim 5, further comprising a compressible lining for placing between the stump and said cast portion to assist in applying mild compression to the stump and maintain a close fit after stump shrinkage.

11. The lower limb prosthetic assembly of claim 10, wherein said compressible lining is formed of foam rubber having a thickness of from about 0.5 to about 1 inch.

12. The lower limb prosthetic assembly of claim 10, wherein said compressible lining comprises a flat flower-like piece of compressible material having a substantially circular middle to be placed over the end of the stump and having a plurality of petals to be overlappingly folded over the stump.

13. The lower limb prosthetic assembly of claim 12, wherein said compressible lining has six petals.

14. A removable, size-adjustable rigid dressing for placement around a patient's amputation stump, comprising:

a substantially stump-shaped rigid cast portion for placement around said stump, said cast portion being open-ended at the top and shaped to enclose and secure around the stump at its bottom to apply mild compression for suppressing edema of the stump, said cast portion having four interconnecting separatable shell sections with vertical separations extending from one end of the cast portion to the other end of the cast portion wherein said vertical separations are substantially located at 0°, 90°, 180°, and 270° of the circumference of said cast portions, said cast portion having
  (a) locking means at two of the opposing vertical separations so that said cast portion can be separated into two pieces for removal and inspection of the physiological status of the stump and rejoined and locked onto the patient's stump, and
  (b) sizing means between the other two opposing vertical separations so that said cast portion can be adjusted in size circumferentially.

15. The lower limb prosthetic assembly of claim 14, further comprising a compressible lining for placing between the stump and said cast portion to assist in applying mild compression to the stump and maintain a close fit after stump shrinkage.

16. The lower limb prosthetic assembly of claim 15, wherein said compressible lining comprises a flat flower-like piece of compressible material having a substantially circular middle to be placed over the end of the stump and having a plurality of petals to be overlappingly folded over the stump.

17. In a lower limb prosthetic assembly for immediate post-operative amputation applications having a weight-bearing prosthetic device which includes a foot-ankle assembly; an adjustable endoskeletal shank attached to said foot-ankle assembly including vertical and horizontal adjustment means for adapting said weight-bearing prosthetic device to a particular patient; medial and lateral uprights extending upwardly from said endoskeletal shank for supporting the patient, said uprights having upper and lower sections connected by a knee joint; an open ended quadrilateral thigh socket attached to and located between the medial and lateral uprights, said thigh socket having an ischial weight-bearing shelf for supporting the patient without contact to the wound; and a suspension means for supporting said prosthetic device of the patient, said suspension means being attachable around the torso of the patient, wherein the improvement comprises:

an independent removable, size-adjustable rigid dressing for placement around the patient's amputation stump below said quadrilateral thigh socket, said rigid dressing including a substantially stump-shaped rigid cast portion for placement around said stump, said cast portion being open-ended at the top and shaped to enclose and secure around the stump at its bottom to apply mild compression for suppressing edema of the stump, said cast portion having
  (a) two separatable vertical half shells wherein each half shell has two vertically-separatable overlapping sections including an outside overlapping section and an inside overlapping section, said overlapping sections slidably adjustable for adaptation to different size stumps, each of the outside overlapping sections having a horizontal slot,
  (b) sizing means on said cast portion for adjusting said cast portion in size circumferentially and for holding said overlapping sections together, said sizing means including fastening adjustment means slidably extending through each of said horizontal slots for tightening said overlapping sections securely together, and
  (c) locking means for securing said two half shells together around the amputation stump.

18. In a lower limb prosthetic assembly for immediate post-operable amputation applications having a weight-bearing prosthetic device which includes a foot-ankle assembly; an adjustable endoskeletal shank attached to said foot-ankle assembly including vertical and horizontal adjustment means for adapting said weight-bearing prosthetic device to a particular patient; medial and lateral uprights extending upwardly from said endoskeletal shank for supporting the patient, said uprights having upper and lower sections connected by a knee joint; an open ended quadrilateral thigh socket attached to and located between the medial and lateral uprights, said thigh socket having an ischial weight-bearing shelf for supporting the patient without contact to the wound; and a suspension means for supporting said prosthetic device to the patient, said suspension means being attachable around the torso of the patient, wherein the improvement comprises:
  an independent removable, size-adjustable rigid dressing for placement around the patient's amputation stump below said quadrilateral thigh socket, said rigid dressing including
  a substantially stump-shaped rigid cast portion for placement around said stump, said cast portion being open-ended at the top and shaped to enclose and secure around the stump at its bottom to apply mild compression for suppressing edema of the stump, said cast portion having
    (a) two separatable vertical half shells wherein each half shell has two vertically-separatable overlapping sections including an outside overlapping section and an inside overlapping section, said overlapping sections slidably adjustable for adaptation to different size stumps,
    (b) sizing means on said cast portion for adjusting said cast portion in size circumferentially and for holding said overlapping sections together,
    (c) locking means for securing said two half shells together around the amputation stump, and
    (d) a compressible lining for placing between the stump and said cast portion to assist in applying mild compression to the stump and maintain a close fit after stump shrinkage, said compressible lining including a flat flower-like piece of compressible material having a substantially circular middle to be placed over the end of the stump and having a plurality of petals to be overlappingly folded over the stump, wherein the thickness of each of said petals is tapered toward an adjacent petal so that when said petals are folded on the stump and overlapped the overlapped petals cover the stump with a substantially uniform thickness of compressible material.

19. A lower limb prosthetic assembly for immediate post-operative amputation applications comprising:
  (A) a weight-bearing prosthetic device including
    (i) a foot-ankle assembly;
    (ii) an adjustable endoskeletal shank attached to said foot-ankle assembly including vertical and horizontal adjustment means for adapting said weight-bearing prosthetic device to a particular patient;
    (iii) medial and lateral uprights extending upwardly from said endoskeletal shank for supporting the patient, said uprights having upper and lower sections connected by a knee joint;
    (iv) an open ended quadrilateral thigh socket attached to and located between the medial and lateral uprights, said thigh socket having an ischial weight-bearing shelf for supporting the patient without contact to the wound;
    (v) a suspension means for supporting said weight-bearing prosthetic device on the patient, said suspension means being attachable around the torso of the patient; and
  (B) an independent removable, size-adjustable rigid dressing for placement around the patient's amputation stump below said quadrilateral thigh socket, said rigid dressing including
    (i) a substantially stump-shaped rigid cast portion for placement around said stump, said cast portion being open-ended at the top and shaped to enclose and secure around the stump at its bottom to apply mild compression for suppressing edema of the stump, said cast portion having
      (a) two vertical half shells wherein each half shell has two vertically-separatable overlapping sections slidably adjustable for adaption to different size stumps,
      (b) belt-like locking means for securing said two half shells together around the amputation stump, and
      (c) sizing means on said cast portion for adjusting said cast portion in size circumferentially and for holding said overlapping sections together, wherein each of said outside overlapping sections has a horizontal slot, said sizing means including fastening adjustment means slidably extending through each of said horizontal slots for tightening said overlapping sections securely together, and
    (ii) a foam rubber compressible lining for placing between the stump and said cast portion to assist in applying mild compression to the stump and maintain a close fit after stump shrinkage, said compressible lining including a flat flower-like piece of compressible material having a substantially circular middle to be placed over the end of the stump and a plurality of petals to be overlappingly folded over the stump, the thickness of each of said petals being tapered toward an adjacent petal so that when said petals are folded on the stump and overlapped the overlapped petals cover the stump with a substantially uniform thickness of compressible material.

20. A removable, size-adjustable rigid dressing for placement around a patient's amputation stump, comprising:
a substantially stump-shaped rigid cast portion for placement around said stump, said cast portion being open-ended at the top and shaped to enclose and secure around the stump at its bottom to apply mild compression for suppressing edema of the stump, said cast portion having
(a) two separatable vertical half shells wherein each half shell has two vertically-separatable overlapping sections including an outside overlapping section and an inside overlapping section, said overlapping sections slidably adjustable for adaptation to different size stumps,
(b) sizing means on said cast portion for adjusting said cast portion in size circumferentially and for holding said overlapping sections together, and
(c) locking means for securing said two half shells together around the amputation stump.

* * * * *